(12) United States Patent
Toyoda et al.

(10) Patent No.: US 7,157,054 B2
(45) Date of Patent: Jan. 2, 2007

(54) MEMBRANE TYPE GAS SENSOR AND METHOD FOR MANUFACTURING MEMBRANE TYPE GAS SENSOR

(75) Inventors: Inao Toyoda, Anjo (JP); Yasutoshi Suzuki, Okazaki (JP)

(73) Assignee: Denso Corporation, Kariya (JP)

( * ) Notice: Subject to any disclaimer, the term of this patent is extended or adjusted under 35 U.S.C. 154(b) by 567 days.

(21) Appl. No.: 10/211,259

(22) Filed: Aug. 5, 2002

(65) Prior Publication Data

US 2003/0039586 A1 Feb. 27, 2003

(30) Foreign Application Priority Data

Aug. 27, 2001 (JP) .............................. 2001-256145

(51) Int. Cl.
*B32B 5/02* (2006.01)
*G01P 21/00* (2006.01)
*G21C 17/00* (2006.01)

(52) U.S. Cl. ........................... 422/88; 376/256; 73/1.22

(58) Field of Classification Search ............ 422/88–98; 204/421, 424, 426, 431; 73/1.02; 438/22, 438/48–49, 142, 157, 199, 478, 488, 491
See application file for complete search history.

(56) References Cited

U.S. PATENT DOCUMENTS 4,313,338 A * 2/1982 Abe et al. .................. 73/31.06
5,329,138 A * 7/1994 Mitani et al. .................. 257/42
5,335,549 A    8/1994 Kato
5,345,213 A * 9/1994 Semancik et al. ............. 338/34
5,821,402 A * 10/1998 Okajima et al. ............. 73/23.2
6,111,280 A * 8/2000 Gardner et al. ............. 257/253
6,628,501 B1 * 9/2003 Toyoda ....................... 361/303
6,693,001 B1 * 2/2004 Nishihara et al. ........... 438/199

FOREIGN PATENT DOCUMENTS

| JP | A-58-102144 | 6/1983 |
| JP | A-4-15553 | 1/1992 |
| JP | A-11-6810 | 1/1999 |
| JP | A-2000-65662 | 3/2000 |
| JP | A-2000-230845 | 8/2000 |

* cited by examiner

*Primary Examiner*—Jill Warden
*Assistant Examiner*—Keri A. Moss
(74) *Attorney, Agent, or Firm*—Posz Law Group, PLC

(57) ABSTRACT

A gas sensor includes a semiconductor substrate and a sensing membrane. The sensing membrane is located at the bottom of a recess, which is formed by etching the substrate, and includes a heater, heater extension electrodes, a gas sensitive film, and gas-sensitive-film extension electrodes. A first end of each heater extension electrode is in contact with the heater, and a second end of each heater extension electrode extends outward from the sensing membrane. A first end of each gas-sensitive-film extension electrode is in contact with the gas sensitive film, and a second end of each gas-sensitive-film extension electrode extends outward from the sensing membrane. All of the heater, the heater extension electrodes, and the gas-sensitive-film extension electrodes are made of polycrystalline silicon.

14 Claims, 8 Drawing Sheets

MEMBRANE TYPE GAS SENSOR AND METHOD FOR MANUFACTURING MEMBRANE TYPE GAS SENSOR

CROSS REFERENCE TO RELATED APPLICATION

This application is based on and incorporates herein by reference Japanese Patent Application No. 2001-256145 filed on Aug. 27, 2001.

BACKGROUND OF THE INVENTION

The present invention relates to a gas sensor, in which a gas sensitive film for detecting a gas is located on a membrane supported by a semiconductor substrate, and to a method for manufacturing the gas sensor.

JP-A-58-102144 and JP-B2-2582343, the corresponding US patent of which is U.S. Pat. No. 5,545,300, disclose gas sensors of this kind. The sensors disclosed in the publications include a membrane, which is located at the bottom of a recess that is formed in a semiconductor substrate by etching the semiconductor substrate. The membrane includes a gas sensitive film made of a material such as tin oxide ($SnO_2$) and indium oxide ($In_2O_3$) and a heater that generates heat when being electrified. The sensors also include a pair of gas-sensitive-film extension electrodes, which are respectively connected to the gas sensitive film, and a pair of heater extension electrodes, which are respectively connected to the heater.

In the sensors disclosed in the publications, the heater and the extension electrodes are made of a metal having a high melting point such as platinum because the temperatures of the heater and the extension electrodes becomes extremely high on the membrane in operation. However, metals having a high melting point such as platinum may become a pollutant in the fabrication processes of ordinary semiconductor microchips such as a C-MOSFET, so it is preferred to avoid using the metals to make the manufacturing process of a gas sensor compatible with that of ordinary semiconductor microchips.

SUMMARY OF THE INVENTION

The present invention has been made in view of the above aspects with an object to provide a membrane type gas sensor, the manufacturing process of which is compatible with that of ordinary semiconductor microchips and to a method for manufacturing the membrane type gas sensor.

In the present invention, a gas sensor includes a semiconductor substrate and a sensing membrane. The sensing membrane is located at the bottom of a recess, which is formed by etching the substrate, and includes a heater, heater extension electrodes, a gas sensitive film, and gas-sensitive-film extension electrodes. A first end of each heater extension electrode is in contact with the heater, and a second end of each heater extension electrode extends outward from the sensing membrane. A first end of each gas-sensitive-film extension electrode is in contact with the gas sensitive film, and a second end of each gas-sensitive-film extension electrode extends outward from the sensing membrane. All of the heater, the heater extension electrodes, and the gas-sensitive-film extension electrodes are made of polycrystalline silicon.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

The present invention will be described in detail with reference to various embodiments.

First Embodiment

Figure 1:
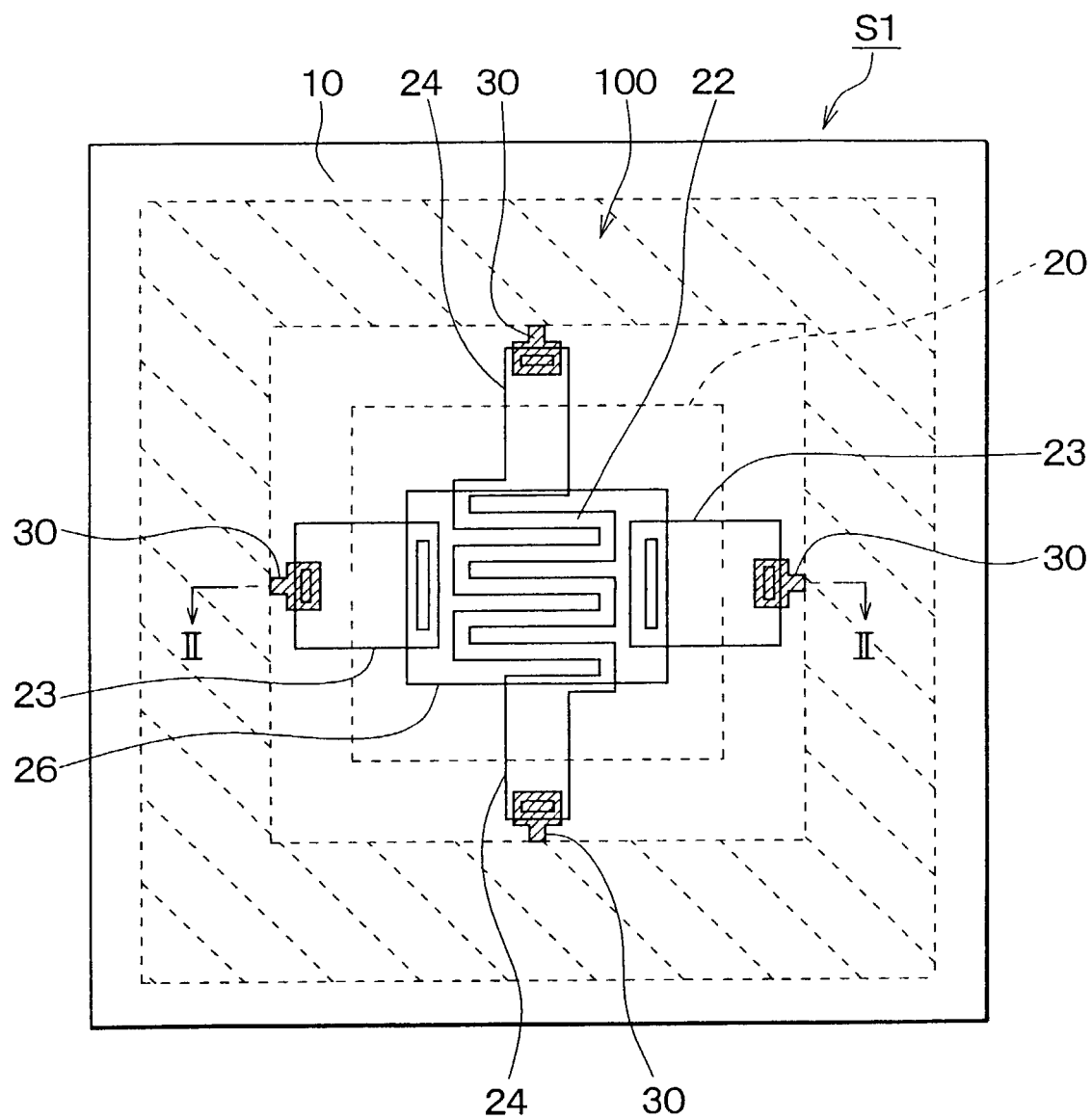
FIG. 1 is a schematic plan view of a gas sensor according to the first embodiment of the present invention.
Figure 2:
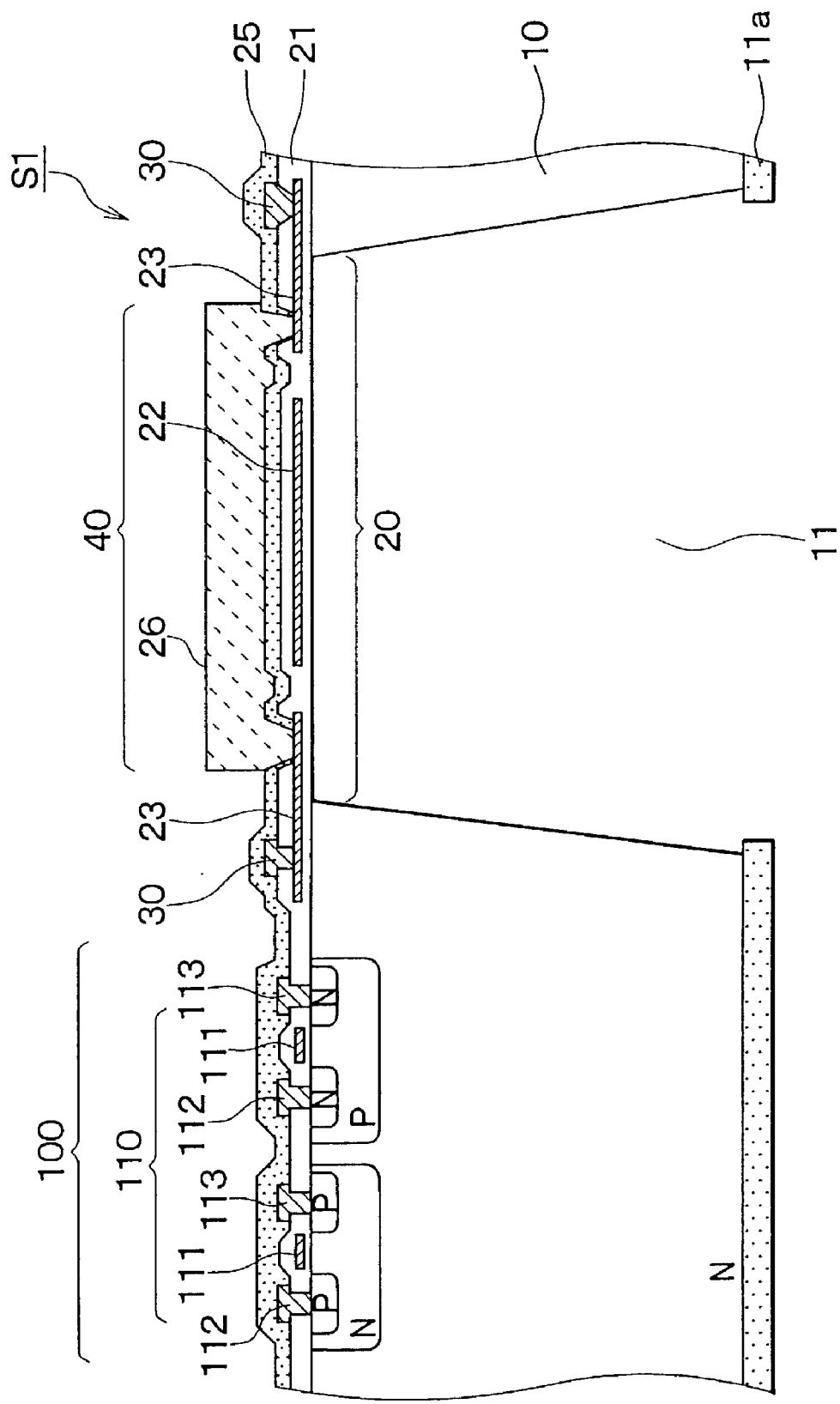
FIG. 2 is a partial cross-sectional view of the gas sensor in FIG. 1 taken along the line II—II.

A gas seneor S1 shown in FIG. 1 is used for detecting a gas such as carbon monoxide (CO), methane ($CH_4$), nitrogen monoxide (NO), and nitrogen dioxide ($NO_2$). As shown in FIGS. 1 and 2, the gas seneor S1 includes a substrate 10 made of n-type silicon and a sensing membrane 20. The sensing membrane 20 is located on one side (e.g., an upper side) of the substrate 10 and makes up the bottom of a recess 11, which is defined by the sensing membrane 20 and an opening that is formed by etching the substrate 10 from an other side (e.g., a lower side) of the substrate 10 that is opposite to the one side.

As shown in FIG. 2, a first insulating film 21, which is made of silicon oxide ($SiO_2$), is located on the upper side of the substrate 10 and at the bottom of the recess 11. A heater 22, a pair of heater extension electrodes 24, and a pair of gas-sensitive-film extension electrodes 23 are made of polycrystalline silicon (poly-Si), which is an ordinarily-used material in semiconductor manufacturing processes, and buried in the first insulating film 21.

A second insulating film 25, which is made of silicon nitride (SiN), is located on the first insulating film 21. A gas sensitive film 26 is located on the second insulating film 25 of the sensing membrane 20. The gas sensitive film 26 is made of a material, the electric resistance of which varies when the material absorbs a gas such as CO, $CH_4$, NO, and $NO_2$. Specifically, the material is a metal oxide type semiconductor such as $SnO_2$ and $In_2O_3$. The sensing membrane 20, which is located as the bottom of the recess 11, includes the first insulating film 21, the heater 22, the heater extension electrodes 24, the gas-sensitive-film extension electrodes 23, the second insulating film 25, and the gas sensitive film 26. The heater 22 generates heat for heating the gas sensitive film 26 when being electrified. The gas-sensitive-film extension electrodes 23 are respectively connected to the gas sensitive film 26, and the heater extension electrodes 24 are respectively connected to the heater 22.

As shown in FIGS. 1 and 2, a plurality of circuit electrodes 30, which are made of aluminum or aluminum alloy, are located around the sensing membrane 20. The circuit electrodes 30 is located between the first insulating film 21 and the second insulating film 25, except at openings located in the insulating films 21, 25. The circuit electrodes 30 may be formed by stacking aluminum or aluminum alloy with other metals. In addition to that, a conductive material used in ordinary semiconductor manufacturing processes such as aluminum-silicon (Al—Si), which contains mainly aluminum and a small quantity, e.g., 0.1 to 0.3%, of silicon, titan (Ti), gold (Au), copper (Cu), and poly-Si may be used for the circuit electrodes 30.

As shown in FIG. 2, a first end of each gas-sensitive-film extension electrode 23 is in electric contact with the gas sensitive film 26 through each opening located in the insulating films 21, 25. A second end of each gas-sensitive-film extension electrode 23 is in electric contact with each circuit electrode 30 through each opening located in the first insulating film 21 outside the sensing membrane 20.

In the gas sensor S1 shown in FIGS. 1 and 2, the heater 22 is patterned to wind beneath the gas sensitive film 26 in the sensing membrane 20 and electrically insulated from the gas sensitive film 26 by the insulating films 21, 25. In the gas seneor S1 shown in FIGS. 1 and 2, the heater extension electrodes 24 and the heater 22 are integrated such that a first end of each heater extension electrodes 24 is connected to the heater 22. Although not shown in FIG. 2, a second end of each heater extension electrode 24 is in electric contact with each circuit electrode 30 through each opening located in the first insulating film 21 outside the sensing membrane 20. As shown FIG. 2, a gas detecting area 40 is the area that is defined by the gas sensitive film 26, so the gas detecting area 40 is located only on the sensing membrane 20 in the gas seneor S1 shown in FIGS. 1 and 2.

In the gas seneor S1 shown in FIGS. 1 and 2, a plurality of circuit components 100, which are electrically connected to the circuit electrodes 30, are located in the hatched area around the sensing membrane 20 in FIG. 1. The circuit components 100 are formed for electrifying the heater 22 through the circuit electrodes 30 and processing the electric signal that is generated at the gas sensitive film 26 in the form of resistance variation. As shown in FIG. 2, the circuit components 100 include a complementary MOSFET 110 (C-MOSFET), which consists of a P channel MOSFET and an N channel MOSFET. Each MOSFET includes a gate electrode 111, a source electrode 112 that is in contact with a source region, and a drain electrode 113 that is in contact with a drain region.

The electrodes 111, 112, 113 of the C-MOSFET 110 can be formed using materials that are used in the manufacturing processes for ordinary C-MOSFETs. In the gas seneor S1 shown in FIGS. 1 and 2, the gate electrodes 111 is made of poly-Si, which is the same material used for forming the heater 22, the heater extension electrodes 24, and the gas-sensitive-film extension electrodes 23. The source electrodes 112 and the drain electrodes 113 are made of aluminum or aluminum alloy, which is the same material used for forming the circuit electrodes 30. The first and second insulating films 21, 25 respectively function as an interlayer insulating film and a passivation film in the C-MOSFET 110 of the circuit components 100. In FIG. 2, only one C-MOSFET 110 is illustrated. However, as a matter of course, the circuit components 100 may include a plurality of C-MOSFETs 110, and moreover, the circuit components 100 may include other transistors such as a bipolar transistor and a Bi-CMOS transistor.

Figure 3A:
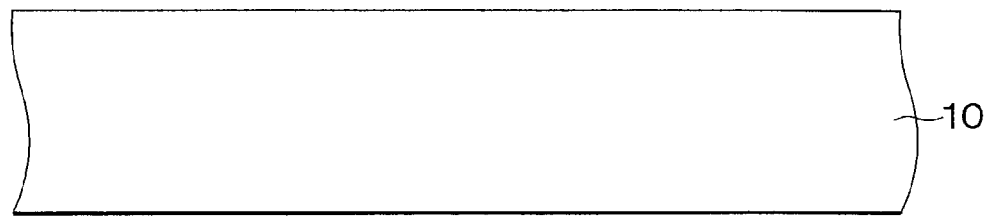
FIGS. 3A to 3C are partial cross-sectional views showing sequential steps of the fabrication process of the gas sensor according to the first embodiment.
Figure 3B:
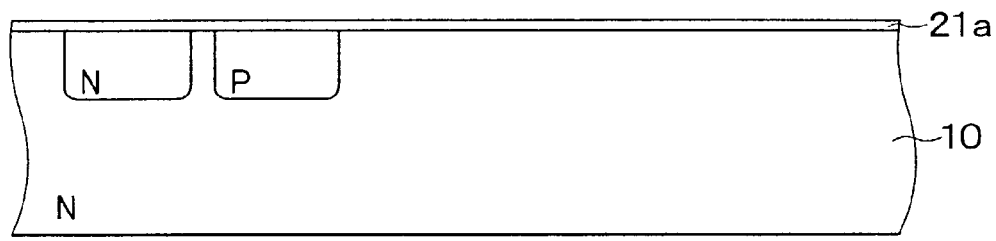
Figure 3C:
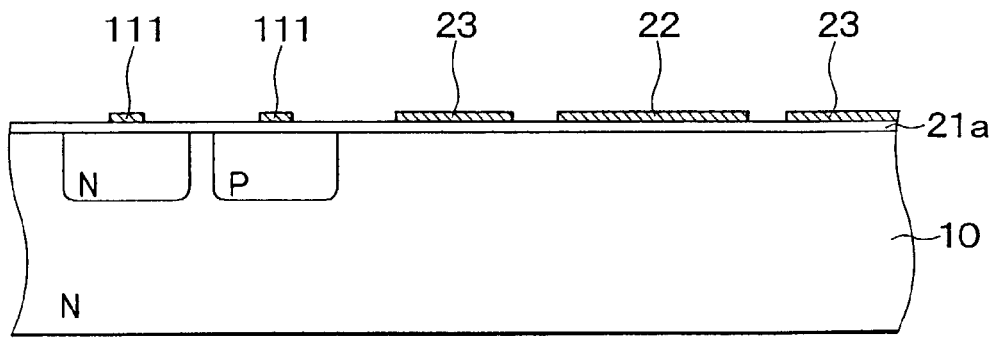

The gas sensor S1 in FIGS. 1 and 2 is manufactured using the n-type silicon substrate 10 shown in FIG. 3A as follows. Firstly, a thermal oxide film 21a is thermally formed on the upper side of the substrate 10, and well regions for the C-MOSFET 110 are formed by ion implantation through the thermal oxide film 21a and thermal diffusion, as shown in FIG. 3B. Then, a poly-Si film is deposited by CVD method on the thermal oxide film 21a, and the heater 22, the heater extension electrodes 24, the gas-sensitive-film extension electrodes 23, and the gate electrode 111 are simultaneously patterned out of the poly-Si film, as shown in FIG. 3C, in which the heater extension electrodes 24 is not illustrated.

Figure 4A:
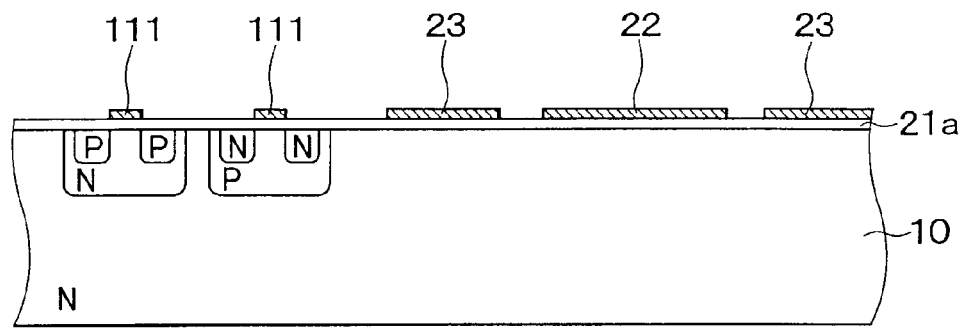
FIGS. 4A to 4C are partial cross-sectional views showing the next sequential steps of the fabrication process following FIG. 3C.
Figure 4B:
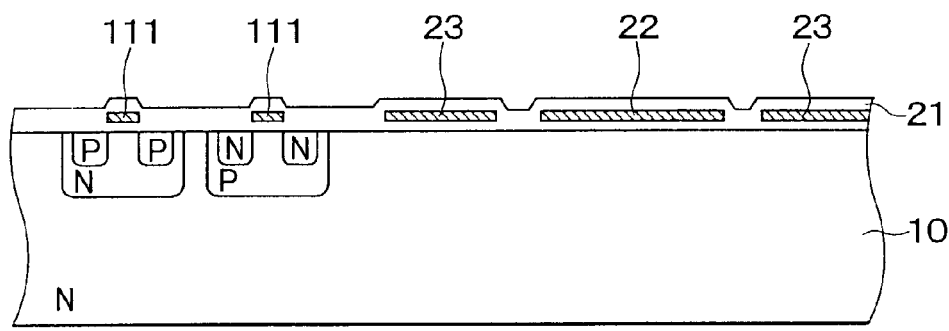
Figure 4C:
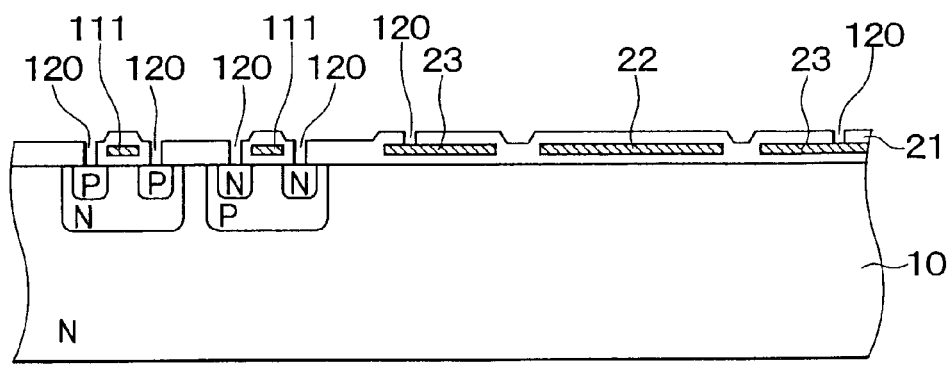

Next, the source and drain regions are formed by ion implantation and thermal diffusion, as shown in FIG. 4A. Then, a silicon oxide film is formed by CVD method, as shown in FIG. 4B. The silicon oxide film and the thermal oxide film 21a are integrated and make up the silicon oxide film 21, which is the first insulating film 21. Subsequently, as shown in FIG. 4C, contact holes 120 are formed in the first insulating film 21 by photolithography and etching to electrically connect the source regions to the source electrodes 112, the drain regions to the drain electrodes 113, and all of the heater 22, the heater extension electrodes 24, the gas-sensitive-film extension electrodes 23 to the circuit electrodes 30.

Figure 5A:
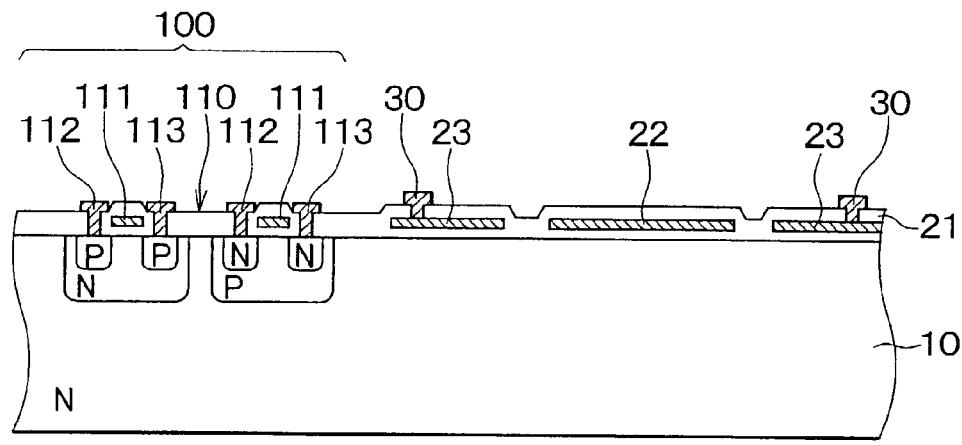
FIGS. 5A to 5C are partial cross-sectional views showing the next sequential steps of the fabrication process following FIG. 4C.
Figure 5B:
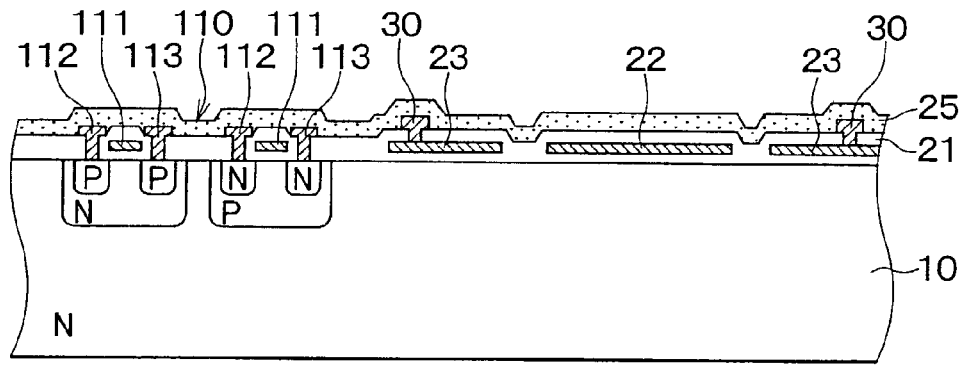
Figure 5C:
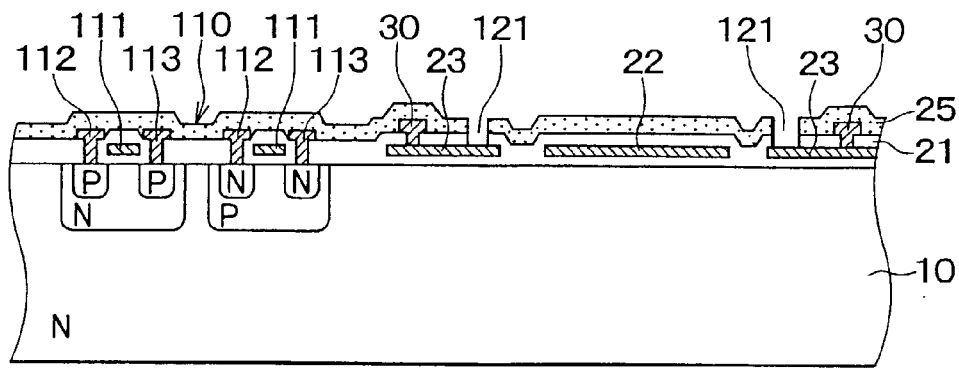
Figure 6A:
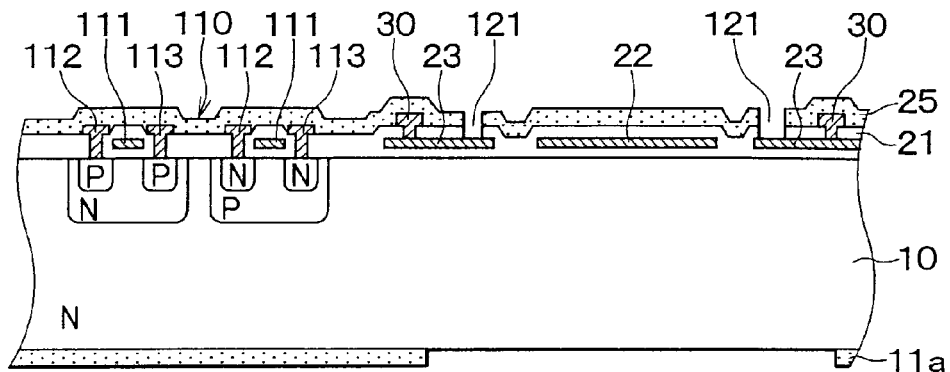
FIGS. 6A to 6C are partial cross-sectional views showing the next sequential steps of the fabrication process following FIG. 5C.

The source electrodes 112, the drain electrodes 113, and the circuit electrodes 30 are formed from an aluminum or aluminum alloy film, which is deposited by sputtering, as shown in FIG. 5A. At the same time, although not shown, other wirings for the circuit components 100 are formed. Next, the silicon nitride film 25, which is the second insulating film 25, is formed by CVD, as shown in FIG. 5B. Next, as shown in FIG. 5C, contact holes 121 are formed in the silicon oxide film 21 and the silicon nitride film 25 at predetermined positions by photolithography and etching for electrically connecting the gas-sensitive-film extension electrodes 23 to the gas sensitive film 26. At the same time, although not shown, other contact holes are formed in the silicon oxide film 21 and the silicon nitride film 25 at the positions of bonding pads for wire bonding in the circuit components 100. Next, an etching mask 11a, which is made of silicon nitride, is formed on the lower side of the silicon substrate 10 except at the area where the recess 11 is formed, as shown in FIG. 6A. The above steps shown in FIGS. 1A to 6A are conducted by using a production line for ordinary semiconductor microchips.

Figure 6B:
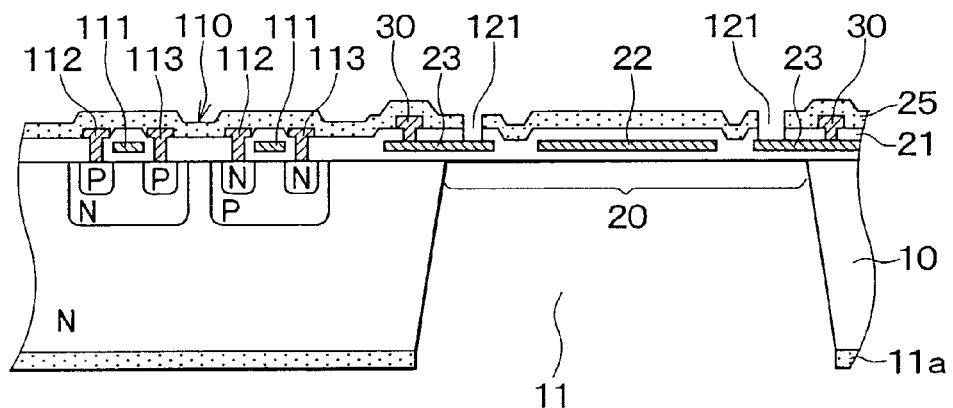

Then, the recess 11 is formed at the position corresponding to the heater 22, the heater extension electrodes 24, and the gas-sensitive-film extension electrodes 23 by anisotropically etching the silicon substrate 10 from the lower side using an etchant such as an alkaline aqueous solution containing potassium hydroxide (KOH), as shown in FIG. 6B. An opening is formed in the silicon substrate 10, and a preliminary membrane, which makes up the bottom of the recess 11, is formed at an end of the opening by the etching.

Figure 6C:
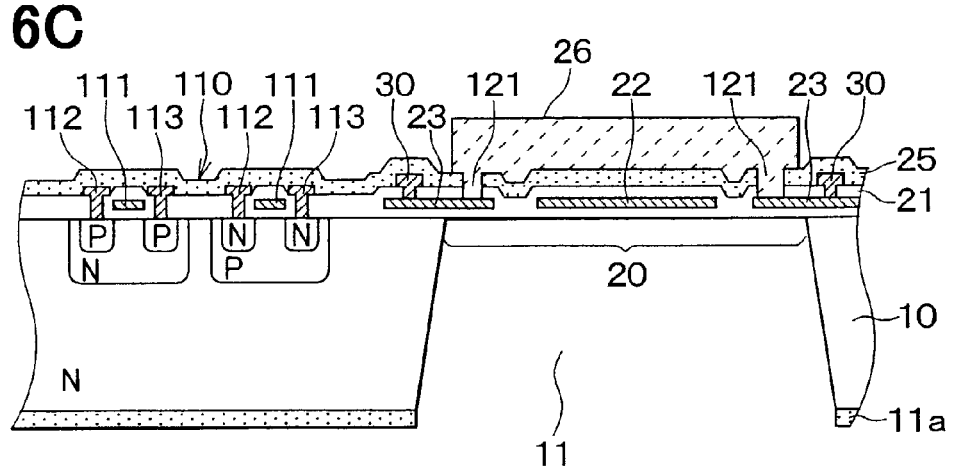

Then, as shown in FIG. 6C, in a production line different from the one used for the above steps, the gas sensitive film 26 is formed by printing a paste that contains $SnO_2$ or $In_2O_3$ on the preliminary membrane and hardening the paste to form the sensing membrane 20 and the gas detecting area 40 on the upper side of the substrate 10. At this stage, the gas seneor S1 shown in FIGS. 1 and 2 is completed.

Metal oxide type semiconductors such as $SnO_2$ and $In_2O_3$ can pollute the fabrication processes of ordinary semiconductor microchips including elements such as the C-MOSFET 110 if they exist in the production line for the semiconductor microchips. However, in the method according to the first embodiment, the gas sensitive film 26 is formed in the different production line after the manufacturing steps shown in FIGS. 1A to 6A for the C-MOSFET 110. Therefore, the C-MOSFET 110 is prevented from being polluted by the metal oxide type semiconductors. Moreover, the manufacturing steps shown in FIGS. 1A to 6A for the C-MOSFET 110 are compatible with the fabrication processes of ordinary semiconductor microchips.

As the material for the gas sensitive film 26, a paste containing metal oxide type semiconductor, the electric resistance of which varies in response to the concentration of a detected gas, is preferably used. The paste that enables the formation of the gas sensitive film 26 by printing and hardening at a temperature lower than 450° C. is more preferably used because the electronic characteristics of the circuit components 100 remain unaffected at a temperature lower than 450° C. Finally, the gas seneor S1 in FIGS. 1 and 2 is electrically connected to an outside circuit by wire bonding the bonding pads and corresponding pads in the outside circuit.

The gas seneor S1 in FIGS. 1 and 2 operates as follows. The heater 22 is heated by electrifying the heater 22 from the circuit components 100. The sensing membrane 20 is heated to a temperature between 300° C. and 600° C. by the heat generated at the heater 22 to provide the gas sensitive film 26. Except for the sensing membrane 20, the temperature of the gas seneor S1 remains lower than 120 because the heat is released through the silicon substrate 10. Therefore, there is no thermal leak at PN junctions between the well regions and no thermal deterioration of the wirings for the circuit components 100.

The electric resistance of the gas sensitive film 26 varies in response to the concentration of a detected gas such as $CO$, $CH_4$, $NO$, and $NO_2$ in the atmosphere where the sensor S1 is placed. The electric resistance variation of the gas sensitive film 26 is processed by the circuit components 100 to provide a predetermined form of signal, the intensity of which corresponds to the concentration of the detected gas. For example, the electric resistance variation of the gas sensitive film 26 is transduced to a potential variation by the C-MOSFET 110 in the circuit components 100, and the potential variation is amplified and corrected to output the signal in response to the concentration of the detected gas.

In the gas sensor S1 in FIGS. 1 and 2, all of the heater 22, the heater extension electrodes 24, and the gas-sensitive-film extension electrodes 23 are made of poly-Si, instead of platinum, which may become a pollutant in the fabrication processes of ordinary semiconductor microchips such as a C-MOSFET. Therefore, the manufacturing process of the gas sensor S1 is further compatible with that of ordinary semiconductor microchips. In addition, the gas-sensitive-film extension electrodes 23 and the heater extension electrodes 24 are electrically connected to the circuit electrodes 30, which are located outside the sensing membrane 20, and the circuit electrodes 30 are electrically connected to the circuit components 100, which are also located outside the sensing membrane 20. Therefore, the gas detecting area 40 and the circuit components 100 are relatively readily integrated into the gas sensor S1 in FIGS. 1 and 2.

The gate electrodes 111 of the C-MOSFET 110, which is included in the circuit components 100, are made of poly-Si. Therefore, the manufacturing process of the gas sensor S1 has an advantage of being able to consolidate the material for the gate electrodes 111 and the material for the heater 22, the heater extension electrodes 24, and the gas-sensitive-film extension electrodes 23 and of being able to form simultaneously the gate electrodes 111, the heater 22, the heater extension electrodes 24, and the gas-sensitive-film extension electrodes 23.

Second Embodiment

Figure 7:
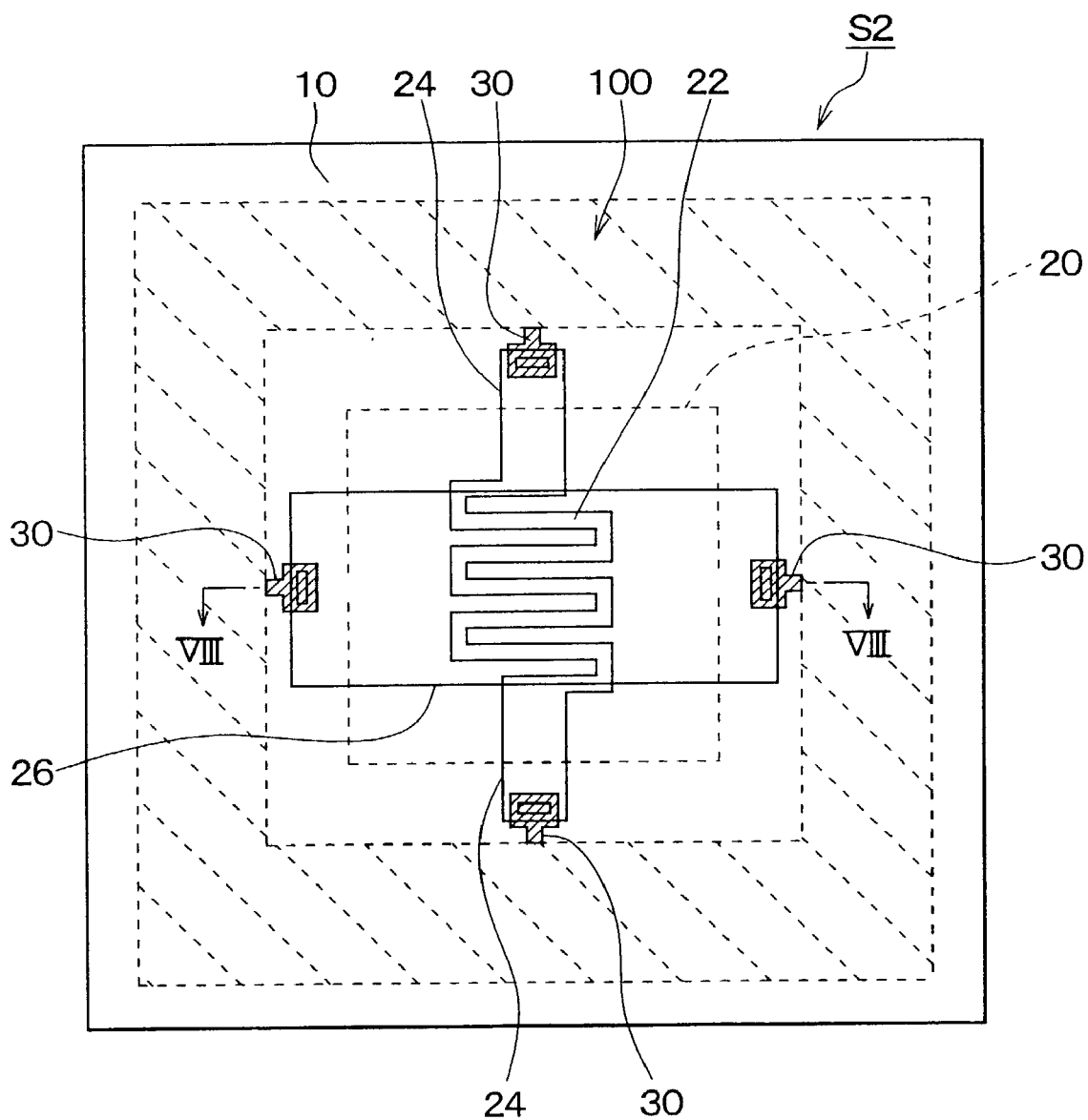
FIG. 7 is a schematic plan view of a gas sensor according to the second embodiment of the present invention.
Figure 8:
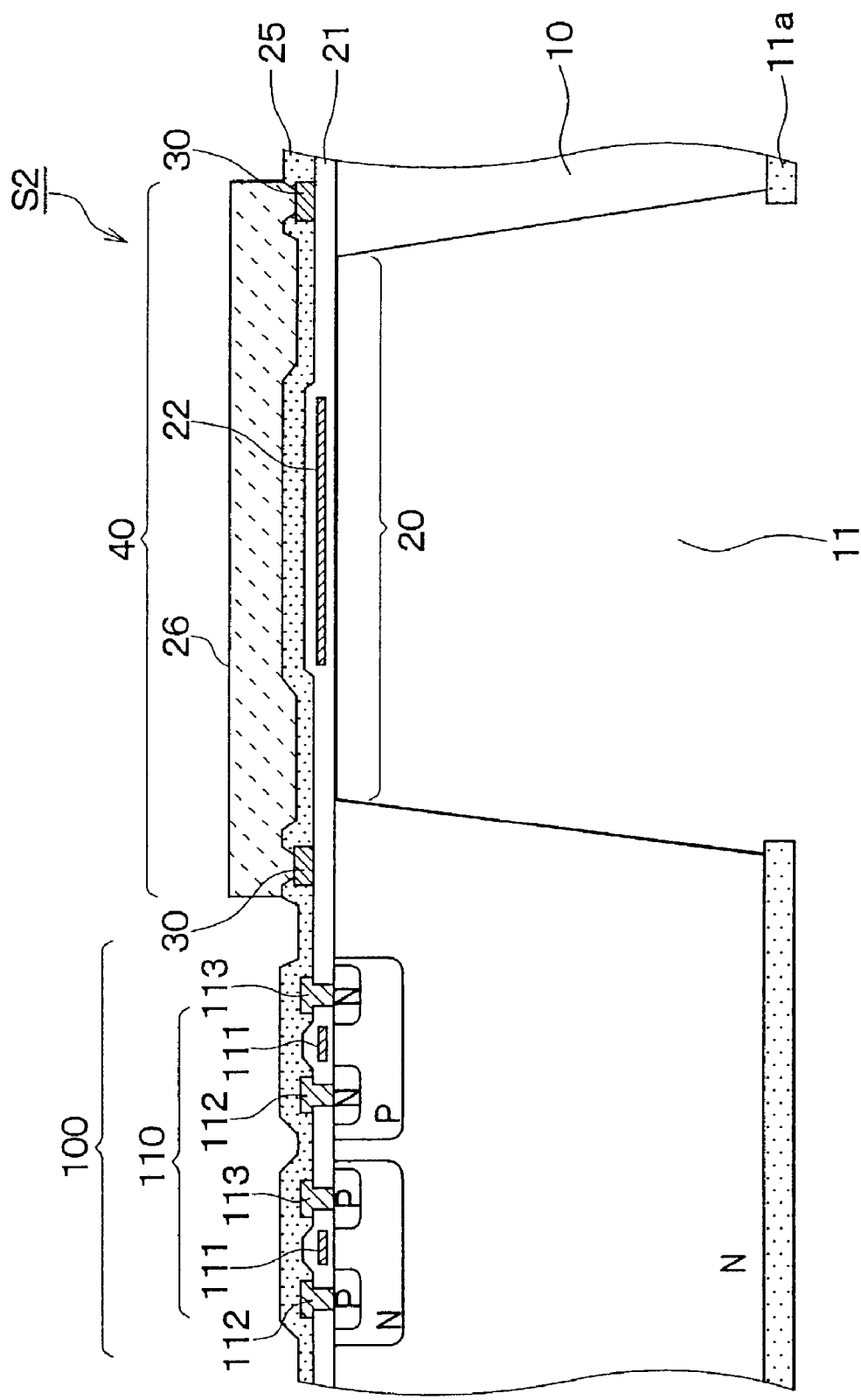
FIG. 8 is a partial cross-sectional view of the gas sensor in FIG. 7 taken along the line VIII—VIII.

As shown in FIG. 7, a gas sensor S2 according to the second embodiment has no gas-sensitive-film extension electrodes 23. Instead, a gas sensitive film 26 extends outward from a sensing membrane 20 to be directly connected to circuit electrodes 30. Heater extension electrodes 24 electrically connect heater 22 and circuit electrodes 30 in the gas sensor S2 in the same manner as in the gas sensor S1 according to the first embodiment. As shown in FIG. 8, the gas sensitive film 26 is electrically connected to the circuit electrodes 30 through contact holes that are located in a silicon nitride film 25 outside the sensing membrane 20. The gas sensor S2 in FIGS. 7 and 8 according to the second embodiment is manufactured using substantially the same manufacturing steps as for the gas sensor S1 in FIGS. 1 and 2, except for the steps shown in FIG. 3C, FIG. 4C, and FIG. 5C. In the manufacturing process for the gas sensor S2, only the heater 22 and the heater extension electrodes 24 are patterned out of a poly-Si film at the step shown in FIG. 3C, and contact holes 120 are not formed in silicon oxide film 21 at the positions corresponding to the circuit electrodes 30 at the step shown in FIG. 4C, and contact holes 121 are formed in silicon nitride film 25 at the positions corresponding to the circuit electrodes 30 at the step shown in FIG. 5C.

As well as the gas sensor S1 in FIGS. 1 and 2, the heater 22 and the heater extension electrodes 24 are made of poly-Si in the gas sensor S2 in FIGS. 7 and 8. Therefore, the manufacturing process of the gas sensor S2 as well is compatible with that of ordinary semiconductor microchips. The gas sensor S2 provides substantially the same effect as the gas sensor S1. However, there are the following differences between the gas sensors S1 and S2. The sensing membrane 20 of the gas seneor S1 has a better heat holding capability than that of the gas sensor S2 because the periphery of the sensing membrane 20 of the gas sensor S2 is thicker than that of the gas seneor S1 due to the extended gas sensitive film 26 and heat releases more readily.

The gas sensitive film 26 and the circuit electrodes 30 are connected with the gas-sensitive-film extension electrodes 23, which is made of poly-Si, in the gas sensor S1 while the gas sensitive film 26 are directly connected to the circuit electrodes 30 in the gas sensor S2. Therefore, the sensitivity of the gas seneor S1 is affected by the electric resistance characteristics of the gas-sensitive-film extension electrodes 23 and the sensitivity of the gas seneor S1 needs to be corrected while that of the gas sensor S2 does not.

Modification

The gas seneor S1 in FIGS. 1 and 2 and the gas sensor S2 in FIGS. 7 and 8 do not necessarily need to include the circuit components 100, which electrify the heater 22 through the circuit electrodes 30 and process the electric signal that is generated at the gas sensitive film 26. The circuit components 100 may be formed separately from the gas sensors S1, S2 as an external circuit, and in that case, the gas detecting area 40 and the external circuit may be electrically connected by wire bonding.

What is claimed is:

1. A gas sensor comprising:
   a semiconductor substrate, which has an opening; and
   a sensing membrane, which is located at an end of the opening to make up a recess in combination with the opening and includes:

a gas sensitive film;

a heater made of polycrystalline silicon;

a pair of gas-sensitive-film extension electrodes made of polycrystalline silicon, wherein a first end of each gas-sensitive-film extension electrode is in electric contact with the gas sensitive film and a second end of each gas-sensitive-film extension electrode extends outward from the sensing membrane; and a pair of heater extension electrodes made of polycrystalline silicon, wherein a first end of each heater extension electrode is in electric contact with the heater and a second end of each heater extension electrode extends outward from the sensing membrane, wherein the gas-sensitive-film extension electrodes and the heater are provided on a same layer of the semiconductor substrate.

2. The gas sensor in claim 1 including a plurality of circuit electrodes, which are made of a metal and located outside the sensing membrane, wherein the gas-sensitive-film extension electrodes and the heater extension electrodes are in electric contact with the circuit electrodes outside the sensing membrane.

3. The gas sensor in claim 2, wherein the circuit electrodes are made of aluminum or aluminum alloy.

4. The gas sensor in claim 2 further comprising circuit components, which are located outside the sensing membrane and are in electric contact with the circuit electrodes, wherein the circuit components electrify the heater through the circuit electrodes and are configured to facilitate processing an electric signal that is generated at the gas sensitive film to provide an output signal.

5. The gas sensor in claim 4, wherein the circuit components include a C-MOSFET.

6. The gas sensor in claim 5, wherein gate electrodes of the C-MOSFET are made of polycrystalline silicon.

7. A gas sensor comprising:

a semiconductor substrate, which has an opening;

a sensing membrane, which is located at an end of the opening to make up a recess in combination with the opening and includes:

a gas sensitive film, which extends to an outside of the opening;

a heater made of polycrystalline silicon; and a pair of heater extension electrodes made of polycrystalline silicon, wherein a first end of each heater extension electrode is in electric contact with the heater and a second end of each heater extension electrode extends outward from the sensing membrane; and a plurality of circuit electrodes, which are made of a metal and located outside the sensing membrane, wherein the heater extension electrodes are in electric contact with the circuit electrodes outside the sensing membrane, and wherein the gas sensitive film is provided with a pair of film electrodes positioned entirely outside the sensing membrane, which are directly connected to the circuit electrodes.

8. The gas sensor in claim 7, wherein the circuit electrodes are made of aluminum or aluminum alloy.

9. The gas sensor in claim 7 further comprising outside electric circuit components, which are located outside the sensing membrane and are in electric contact with the circuit electrodes, wherein the outside components electrify the heater through the circuit electrodes and are configured to facilitate processing an electric signal that is generated at the gas sensitive film and to produce an output signal.

10. The gas sensor in claim 9, wherein the outside electric components include a C-MOSFET.

11. The gas sensor in claim 10, wherein gate electrodes of the C-MOSFET are made of polycrystalline silicon.

12. The gas sensor in claim 7, wherein the gas sensitive film has a dimension in an extending direction, which is larger than a dimension of the sensing membrane in the extending direction.

13. The gas sensor in claim 1, wherein the sensing membrane includes a plurality of layers.

14. A gas sensor comprising:

a semiconductor substrate, which has an opening portion;

a gas sensitive film provided to cover at least a part of the opening portion;

a heater made of polycrystalline silicon;

a pair of film electrodes made of polycrystalline silicon, wherein each film electrode has a first end electrically connected to the gas sensitive film and a second end extending outward from the opening; and a pair of heater electrodes made of polycrystalline silicon, wherein each heater electrode has a first end electrically connected with the heater and a second end extending outward from the opening, wherein the film electrodes and the heater are provided on a single layer on the semiconductor substrate.

* * * * *